US00PP24059P2

(12) United States Plant Patent
Andrusiv

(10) Patent No.: US PP24,059 P2
(45) Date of Patent: Dec. 3, 2013

(54) ***BERBERIS* PLANT NAMED 'GOLDEN DREAM'**

(50) Latin Name: *Berberis thunbergii*
Varietal Denomination: Golden Dream

(75) Inventor: Michal Andrusiv, Litomyal (CZ)

(73) Assignee: Valkplants B.V., Boskoop (NL)

( * ) Notice: Subject to any disclaimer, the term of this patent is extended or adjusted under 35 U.S.C. 154(b) by 98 days.

(21) Appl. No.: 13/506,337

(22) Filed: Apr. 12, 2012

(51) Int. Cl.
*A01H 5/00* (2006.01)

(52) U.S. Cl.
USPC ..... Plt./241

(58) Field of Classification Search
USPC ..... Plt./241
See application file for complete search history.

*Primary Examiner* — Susan McCormick Ewoldt
(74) *Attorney, Agent, or Firm* — Penny J. Aguirre

(57) ABSTRACT

A new cultivar of *Berberis*, 'Golden Dream', that is characterized by its small sized leaves that are yellow-green in color and its moderately compact plant habit with upright branches.

2 Drawing Sheets

Botanical classification: *Berberis thunbergii.*
Cultivar designation: 'Golden Dream'.

RELATED APPLICATIONS

This application is co-pending with U.S. Plant Patent applications filed for cultivars derived from the same breeding program entitled *Berberis* Plant Named 'Orange Dream' (U.S. Plant patent application Ser. No. 13/506,333) and *Berberis* Plant Named 'Red Dream' (U.S. Plant patent application Ser. No. 13/506,332).

BACKGROUND OF THE INVENTION

The present invention relates to a new and distinct cultivar of *Berberis thunbergii*, and will be referred to hereafter by its cultivar name, 'Golden Dream'. 'Golden Dream' is grown for use as a landscape shrub.

The new cultivar arose through an ongoing breeding project by the Inventor in Litomysl, Czech Republic with the objective of selecting new and unique cultivars of *Berberis*. 'Golden Dream' arose from open pollination in 2003 of an unnamed plant of *Berberis thunbergii* from the Inventors breeding program as the female parent. 'Golden Dream' was selected as a single unique plant from the resulting seedlings in 2005.

Asexual reproduction of the new cultivar was first accomplished by the Inventor by softwood stem cuttings in Litomysl, Czech Republic in 2007. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Golden Dream' as a new and distinct cultivar of *Berberis.*

1. 'Golden Dream' exhibits small sized leaves.
2. 'Golden Dream' exhibits foliage that is yellow-green in color.

3. 'Golden Dream' exhibits a moderately compact plant habit with upright branches.

The female parent of 'Golden Dream' differs from 'Golden Dream' in having dark green leaves, a more open growth habit, and broader and larger leaves. 'Golden Dream' can be most closely compared to the cultivars 'Orange Dream', 'Red Dream' 'Admiration' (U.S. Plant Pat. No. 16,921), and 'Aures' (not patented). 'Orange Dream' differs from 'Golden Dream' in having gray-purple to brown leaves, a less compact plant habit, and branches that are arching. 'Red Dream' differs from 'Golden Dream' in having leaves that are brown in color, a less compact plant habit, and branches that are arching. 'Admiration' differs from 'Golden Dream' in having broader larger leaves that are gray-purple to orange-brown in color with thin yellow-green margins and in having an even more dense compact plant habit. 'Aurea' differs from 'Golden Dream' in having yellow leaves and an even more dense compact plant habit.

BRIEF DESCRIPTION OF THE DRAWING

The accompanying colored photographs illustrate the overall appearance and distinct characteristics of the new *Berberis*. The photographs were taken of a plant two years in age as grown in a one-gallon container in Helden, The Netherlands.

The photograph in FIG. 1 provides a view of the plant habit of 'Golden Dream' and the photograph in FIG. 2 provides a close-up view of the foliage of 'Golden Dream'. The colors in the photographs may differ slightly from the color values cited in the detailed botanical description, which accurately describe the colors of the new *Berberis.*

DETAILED BOTANICAL DESCRIPTION OF THE PLANT

Figure 1:
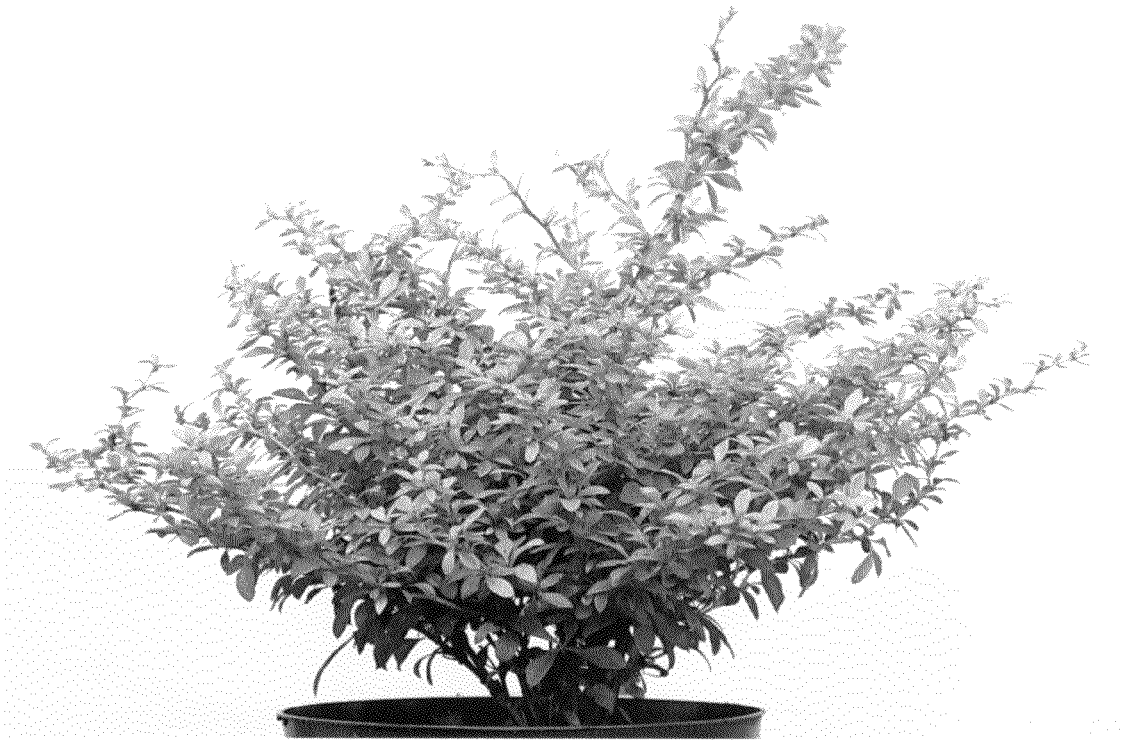
Figure 2:
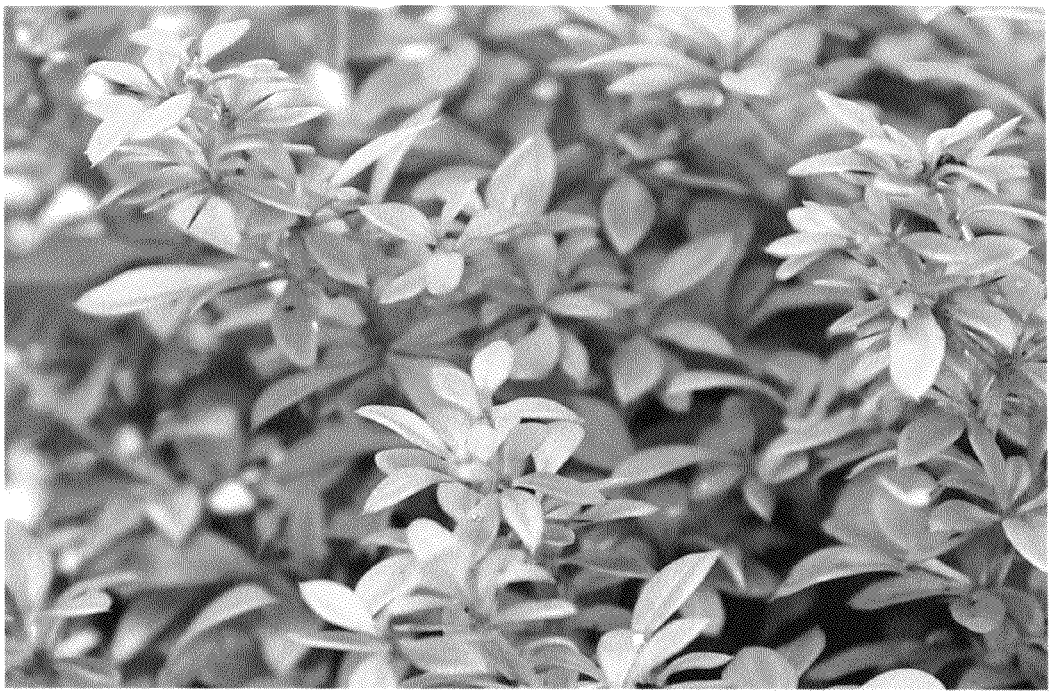

The following is a detailed description of two year-old plants of the new cultivar as grown in one-gallon containers in Helden, The Netherlands. Plants were grown under average day temperatures of 15° C. and average night temperatures of 10° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Perennial deciduous shrub.

*Plant habit*.—Moderately compact plant habit with upright branches.

*Height and spread*.—Reaches about 29.5 cm in height and 38.9 cm in width in a 1.5 liter container.

*Cold hardiness*.—Hardy to at least U.S.D.A. Zone 5.

*Disease resistance*.—Not more susceptible to pests and diseases than other *Berberis*.

*Root description*.—Fibrous, moderate to densely branched.

*Growth rate*.—Moderate.

*Propagation*.—Softwood stem cuttings.

*Rooting*.—Initiate in 28 to 36 days at 17° C. air temperature, a young fully rooted plant is produced in 28 to 36 days at 17 to 19° air temperature (summer).

Stem description:

*Stem size*.—Lateral branches are an average of 14.8 cm in length and 2 mm in diameter.

*Stem shape*.—Round.

*Stem color*.—Young shoots; 171A to 171B, later turning 151D to 151C, mature stems; N199C.

*Stem surface*.—Young and mature stems (both sides) moderately glossy and axially ribbed.

*Stem strength*.—Strong.

*Internode length*.—Average of 9 mm.

*Branching habit*.—Moderate to high with an average of 56 lateral branches.

*Branching aspect*.—Lateral branches an average angle of 50° (vertical=0°).

Foliage description:

*Leaf shape*.—Oblanceolate to obovate.

*Leaf division*.—Simple.

*Leaf base*.—Long attenuate.

*Leaf apex*.—Acute.

*Leaf venation*.—Pinnate.

*Leaf margins*.—Entire.

*Leaf attachment*.—Sessile.

*Leaf arrangement*.—Alternate, clustered.

*Leaf surface*.—Upper surface; smooth and moderately glossy, lower surface; dull.

*Leaf color*.—Upper surface immature foliage; 150A, lower surface immature foliage; 145B, mature foliage upper surface; between 151B and 9B, mature lower surface foliage; 145B.

*Leaf number*.—Average of 6 per cluster at each node, 100 leaves per lateral branch.

*Leaf size*.—Average of 1.9 cm in length and 0.7 cm in width.

*Leaf aspect*.—Held upward at about a 45° angle to horizontal.

*Leaf veins*.—Upper surface; between 151B and 9B, lower surface; N144A.

*Petioles*.—Average of 1 mm in length and 1 mm in diameter, 34B to 34C in color.

*Thorn*.—Below each node is a sharp single thorn; average of 7 mm length and 1 mm in width at base, color; upper side; 171B to 171C, under side; 151D, tip; 200A, base; 34B to 34C, mature thorns; 200A.

Flower description:

*Flowering*.—No flowers have been observed.

*Fruit and seed*.—Seed production has not been observed.

It is claimed:

1. A new and distinct cultivar of *Berberis* plant named 'Golden Dream' as herein illustrated and described.

* * * * *